US010417894B2

(12) United States Patent
Lu

(10) Patent No.: US 10,417,894 B2
(45) Date of Patent: Sep. 17, 2019

(54) ANTI-SLIP CUSHIONING SENSOR MAT

(71) Applicant: Xiamen Sheep Anti-Fatigue Mat Co., Ltd., Xiamen (CN)

(72) Inventor: Xiangyang Lu, Xiamen (CN)

(73) Assignee: XIAMEN SHEEP ANTI-FATIGUE MAT CO., LTD., Xiamen (CN)

( * ) Notice: Subject to any disclaimer, the term of this patent is extended or adjusted under 35 U.S.C. 154(b) by 0 days.

(21) Appl. No.: 15/851,758

(22) Filed: Dec. 22, 2017

(65) Prior Publication Data

US 2019/0197865 A1  Jun. 27, 2019

(51) Int. Cl.
*G08B 21/02* (2006.01)
*G08B 21/04* (2006.01)

(52) U.S. Cl.
CPC ......... *G08B 21/0461* (2013.01); *G08B 21/02* (2013.01); *G08B 21/0438* (2013.01)

(58) Field of Classification Search
CPC .. A47G 27/0406; A47G 27/0412; A47G 9/06; A47G 9/062; A47G 27/02; A47G 27/0212; A63B 2024/004; A63B 6/00; B32B 2471/04; B32B 3/26; B32B 3/266; B32B 3/28; B32B 5/18; B32B 7/08; B32B 37/14; H01H 3/141; G08B 21/00; G08B 21/18; G08B 21/22; G08B 21/24; G08B 21/02; G08B 21/0438; G08B 21/0461; G08B 21/0469; H05K 9/00; H05K 9/007; B05D 1/18
See application file for complete search history.

(56) References Cited

U.S. PATENT DOCUMENTS

| | | | | |
|---|---|---|---|---|
| 5,856,644 A * | 1/1999 | Burgess | ................. | H01H 1/029 200/61.43 |
| 6,121,869 A * | 9/2000 | Burgess | ................. | H01H 3/141 200/511 |
| 2008/0200285 A1* | 8/2008 | Haseth | ................... | A63B 63/00 473/422 |
| 2009/0120777 A1* | 5/2009 | Grzan | .................... | H01H 3/142 200/86 R |
| 2011/0269600 A1* | 11/2011 | Houle | ................ | A63B 23/0458 482/8 |
| 2012/0019387 A1* | 1/2012 | Chiou | ................. | G08B 21/0446 340/573.1 |
| 2016/0023424 A1* | 1/2016 | Lu | ...................... | A47G 27/0212 428/135 |
| 2016/0368239 A1* | 12/2016 | Lu | ........................... | B32B 3/266 |
| 2017/0360234 A1* | 12/2017 | Simon | ................ | A47G 27/0468 |

* cited by examiner

Primary Examiner — Van T Trieu
(74) Attorney, Agent, or Firm — Gokalp Bayramoglu

(57) ABSTRACT

The present invention provides an anti-slip cushioning sensor mat. The mat comprises a PVC leather layer, a polyurethane foaming layer disposed below the PVC leather layer, a sensitive layer disposed below the polyurethane foaming layer; and a rubber layer disposed below the sensitive layer. The sensitive layer further comprises a first flexible thin-film plate, a first conductive layer disposed below the first flexible thin-film plate, an intermediate layer disposed below the first conductive layer, a second conductive layer disposed below the intermediate layer. and a second flexible thin-film plate disposed below the second conductive layer. The present invention also provides an alarm system comprising the anti-slip cushioning sensor mat and a server, and a method for making the anti-slip cushioning sensor mat.

18 Claims, 16 Drawing Sheets

ANTI-SLIP CUSHIONING SENSOR MAT

TECHNICAL FIELD

This invention relates to a mat, especially relates to an anti-slip cushioning sensor mat.

BACKGROUND

Mats are used to provide a comfortable surface to stand on. Current mats used in this field do not have the alarming system to notify health professionals that a patient left his/her position. Even those mats that may include alarming systems, they do not have the capabilities such as determining the exact locations where pressure applied on the mat, no capability of multiple touch detection, no capability of delaying the response of the alarm system, no capability of wireless communication with a central system where health professionals can be notified about patient's position. All these shortcomings of the current art resolved by this invention. The sensor mat of this invention, also known as a sensitive mat, is mainly used for the absence alarm system at hospital and nursing home. The sensor mat may be mounted near a bed, a chair, a wheelchair and so on and is connected with an absence alarm or a nurse calling system. When a patient leaves a bed, a chair, or a wheelchair and set his/her feet on a mat, the patient's weight will be sensed by the sensor mat, and then an alarm will be triggered to inform a nurse that the patient has left his original position and/or fell from where the patient was.

SUMMARY OF THE INVENTION

The object of this invention is to provide an anti-slip cushioning sensor mat, which has the advantages of good elasticity, better foot feels, anti-slip, easy to clean, and presence alarm.

According to one aspect, the present invention provides an anti-slip cushioning sensor mat. The mat comprises a PVC leather layer, a polyurethane foaming layer disposed below the PVC leather layer, a sensitive layer disposed below the polyurethane foaming layer, and a rubber layer disposed below the sensitive layer.

Furthermore, the sensitive layer further may comprise a first flexible thin-film plate, a first conductive layer disposed below the first flexible thin-film plate, a first intermediate layer disposed below the first conductive layer, a second conductive layer disposed below the first intermediate layer, and a second flexible thin-film plate disposed below the second conductive layer.

Furthermore, the first conductive layer may be formed by printing or coating ink made of copper or conductive graphite on the first flexible thin-film plate, and the second conductive layer may be formed by printing or coating the ink on the second flexible thin-film plate.

Furthermore, the first intermediate layer may be provided with a plurality of through holes such that the first conductive layer and the second conductive layer are contacted with each other when the anti-slip cushioning sensor mat is subjected to a vertical force.

Furthermore, the sensitive layer may further comprise a first conductive connecting member connected to the first conductive layer, and a second conducive connecting member connected to the second conductive layer.

Furthermore, the sensitive layer may further comprise a circuit connected to the first conductive connecting member and the second conducive connecting member.

Furthermore, the first conductive connecting member may be disposed between the first conductive layer and the first intermediate layer, and the second conductive connecting member may be disposed between the second conductive layer and the first intermediate layer.

Furthermore, at least one vent may be provided on at least one of the first flexible thin-film plate and the second flexible thin-film plate.

Furthermore, the first intermediate layer may be provided with a plurality of parallel throughout slots such that the first conductive layer and the second conductive layer are contacted with each other when the anti-slip cushioning sensor mat is subjected to a vertical force.

Furthermore, the first conductive layer may include a plurality of wires disposed in a first direction, and the second conductive layer may include a plurality of wires disposed in a second direction, wherein the second direction is different from the first direction.

Furthermore, each of the plurality of wires of the first conductive layer may be connected to a first conductive connecting member, and each of the plurality of wires of the second conductive layer may be connected to a second conductive connecting member.

Furthermore, the plurality of through holes may be aligned with intersections formed by the plurality of wires of the first conductive layer and the plurality of wires of the second conductive layer.

Furthermore, the first conductive connecting member and the second conductive connecting member may be connected to a circuit. The circuit may be programmable to enable and disable each of the plurality of wires of the first conductive layer and each of the plurality of wires of the second conductive layer.

Furthermore, the first conductive layer may include a first flexible conductive section and the second conductive layer includes a second flexible conductive section such that the first flexible conductive section is contacted with the second flexible plate when the sensitive layer is folded at the place where the first flexible conductive section second flexible conductive section are located.

Furthermore, the sensitive layer further comprises: a third flexible thin-film plate, a third conductive layer disposed below the third flexible thin-film plate, a second intermediate layer disposed below the third conductive layer, a fourth conductive layer disposed below the second intermediate layer, and a fourth flexible thin-film plate disposed below the fourth conductive layer.

Furthermore, the first conductive layer is connected with the third conductive layer through at least one first flexible circuit, and the second conductive layer is connected with the fourth conductive layer through at least one second flexible circuit.

According to another aspect, the present invention provides an alarm system. The alarm system comprises an anti-slip cushioning sensor mat configured to detect the presence of a subject and send a signal when the subject is presence, and a server configured to receive the signal and determine whether to sound alarm.

Furthermore, the anti-slip cushioning sensor mat may comprise a PVC leather layer, a polyurethane foaming layer disposed below the PVC leather layer, a sensitive layer disposed below the polyurethane foaming layer, and a rubber layer disposed below the sensitive layer.

Furthermore, the sensitive layer further may comprise a first flexible thin-film plate, a first conductive layer disposed below the first flexible thin-film plate, an intermediate layer disposed below the first conductive layer, a second conductive layer disposed below the intermediate layer, and a second flexible thin-film plate disposed below the second conductive layer.

Furthermore, the intermediate layer may be provided with a plurality of through holes such that the first conductive layer and the second conductive layer are contacted with each other when the anti-slip cushioning sensor mat is subjected to a vertical force.

Furthermore, the sensitive layer may further comprise a first conductive connecting member connected to the first conductive layer, and a second conducive connecting member connected to the second conductive layer. The sensitive layer may further comprise a circuit connected to the first conductive connecting member and the second conducive connecting member.

According to yet another aspect, the present invention provides a method of making an anti-slip cushioning sensor mat. The method comprises the following steps: putting PVC leather into a mold; injecting polyurethane mixed foaming material into the mold to generate a complex multilayer structure including a PVC leather layer and a polyurethane foaming layer; attaching a sensitive layer to the polyurethane foaming layer; and adhering a rubber layer to the sensitive layer.

Hereinafter, this invention will be described in detail combined with the drawings and embodiments.

DETAILED DESCRIPTION OF THE INVENTION

The above and other objects, features, advantages and technical and industrial significance of this invention will be better understood by reading the following detailed description of presently preferred embodiments of the invention, when considered in connection with the accompanying drawings. Elements in the figures are illustrated for simplicity and clarity and have not necessarily been drawn to scale.

Figure 1:
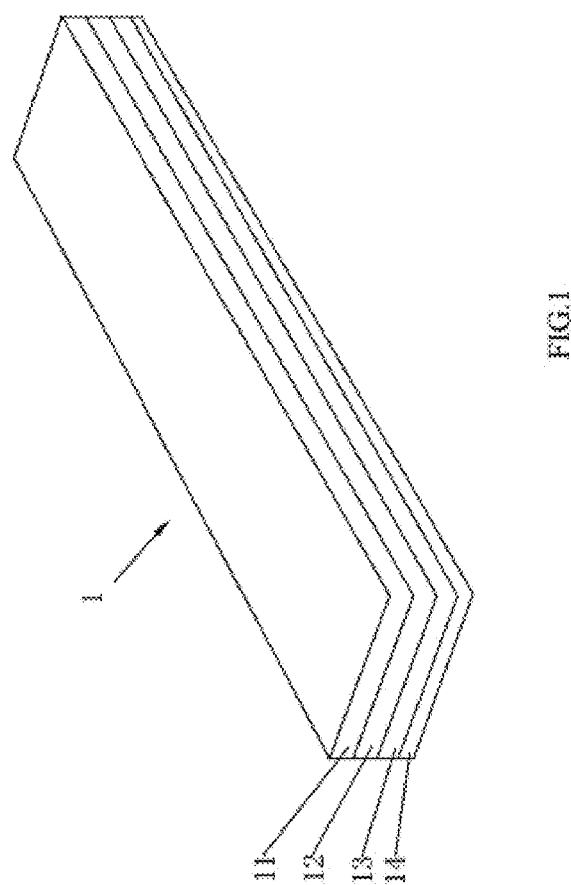
FIG. 1 is a prospective view of an anti-slip cushioning sensor mat according to the first embodiment of the present invention.

FIG. 1 illustrates a prospective view of the anti-slip cushioning sensor mat. As shown in FIG. 1, the anti-slip cushioning sensor mat 1 includes PVC leather layer 11, polyurethane foaming layer 12, sensitive layer 13, and rubber layer 14. The rubber layer 14 is the bottom layer on which the sensitive layer 3 is disposed. The polyurethane foaming layer 12 is disposed above the sensitive layer 13. The PVC leather layer 11, which is also the top layer, is disposed above the polyurethane foaming layer 12.

Figure 2:
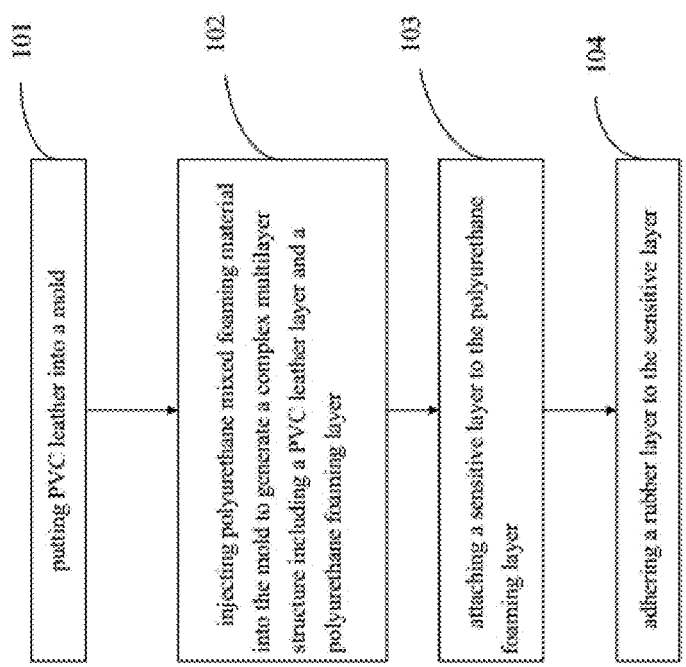
FIG. 2 is a flow chart of a method of making an anti-slip cushioning sensor mat according to the first embodiment of the present invention.

FIG. 2 is a flow chart of a method of making an anti-slip cushioning sensor mat according to the first embodiment of the present invention. As shown in FIG. 2, the anti-slip cushioning sensor mat may be made by the following steps. In step 101, the PVC leather is put into the mold. In step 102, the polyurethane mixed foaming material is injected into the mold to form a complex multilayer structure including the PVC leather layer and the polyurethane foaming layer. In step 103, the sensitive layer is adhered to a side of the complex multilayer structure that exposes the polyurethane foaming layer. In step 104, the rubber layer is adhered to the sensitive layer with glue.

Figure 3:
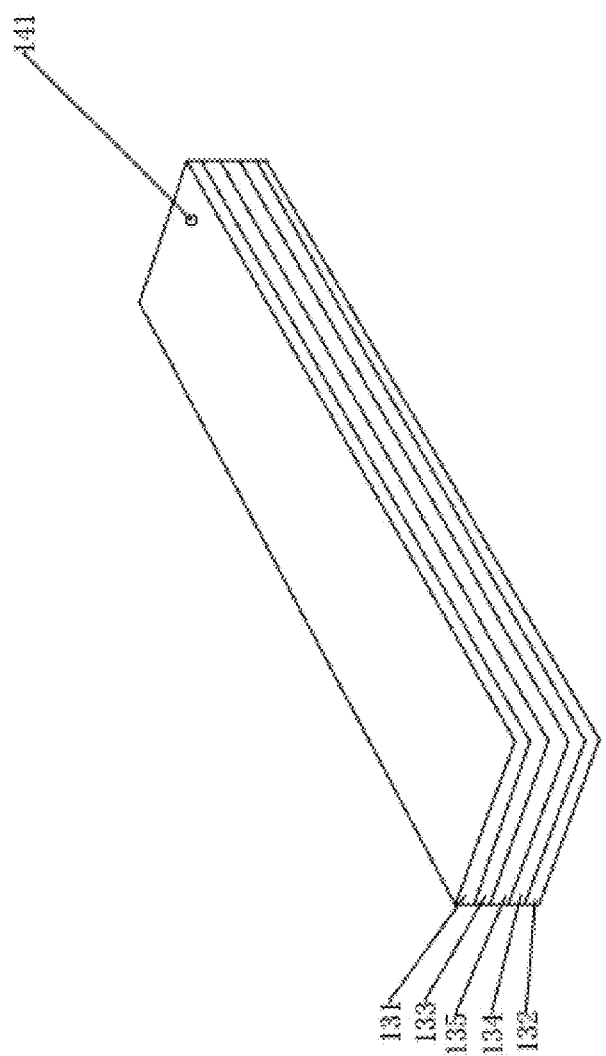
FIG. 3 is a prospective view of a sensitive layer according to the first embodiment of the present invention.

FIG. 3 is a prospective view of a sensitive layer according to the first embodiment of the present invention. As shown in FIG. 3, the sensitive layer 13 includes the first flexible thin-film plate 131, the second flexible thin-film plate 132, the first conductive layer 133, the second conductive layer 134, and the intermediate layer 135. These layers are stacked in the order shown in FIG. 2. The first conductive layer 133 is formed by printing or coating ink, which is made of copper or conductive graphite, on the first flexible thin-film plate 131 and then curing the ink. Similarly, the second conductive layer 134 is formed by printing or coating ink, which is made of copper or conductive graphite, on the first flexible thin-film plate 132 and then curing the ink. The first conductive layer 133 may be formed by using metal conductive traces or transparent conductive traces. More specifically indium tin oxide, zinc oxide, aluminum oxide, aluminum, copper, silver, or gold can be used as conductive traces. The second conductive layer 134 may be formed by using metal conductive traces or transparent metal conductive traces. More specifically indium tin oxide, zinc oxide, aluminum oxide, aluminum, copper, silver, or gold can be used as conductive traces. The intermediate layer 135 is made of low density elastic material, which can make the contact sensing more effective and has a better perform of elastic recovery after being squeezed, compared to the paper plate or hard material used in the existing products.

Figure 4:
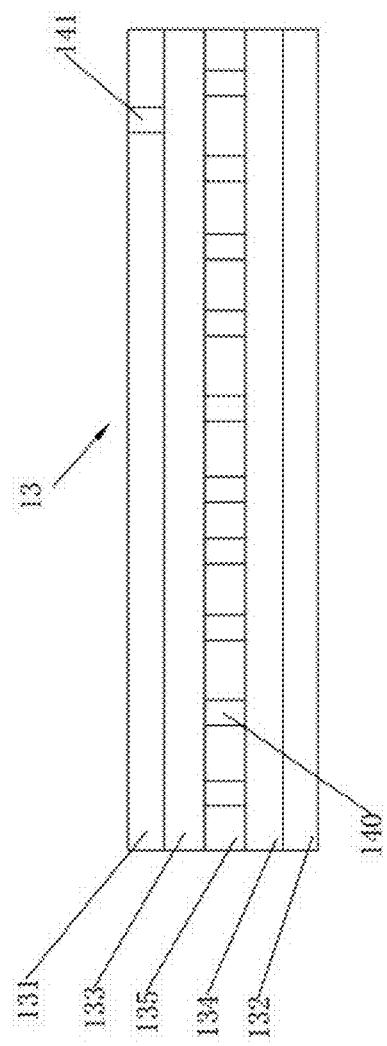
FIG. 4 is a side view of the sensitive layer according to the first embodiment of the present invention.

FIG. 4 is a side view of the sensitive layer according to the first embodiment of the present invention. As shown in FIG. 4, the intermediate layer 135 is provided with a plurality of through holes 140 such that the first conductive layer 133 and the second conductive layer 134 are contacted with each other and thus conduct when the sensitive layer 13 is subjected to an external pressure. In some embodiments, in order to facilitate the discharge and intake of the air in the through holes 140, at least one vent 141 is provided on the flexible thin-film plate. With the vent 141, the air remaining in the sensitive layer 13 during manufacturing can be discharged such that the whole sensitive layer, especially the top/bottom later can be flat and smooth after being adhesive together. In some embodiments, the vent 141 is aligned with any of the through holes or throughout slots in the conductive layers. In some embodiments, the vent 141 can be provided on either of both of the top and bottom layers.

Figure 5:
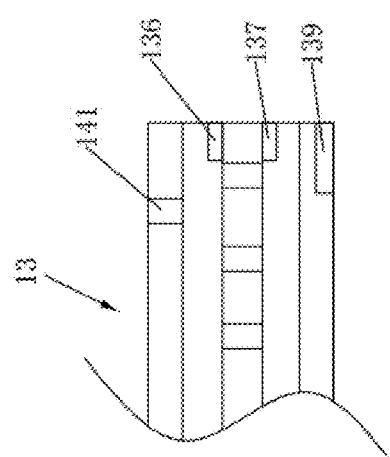
FIG. 5 is a side view of a part of the sensitive layer according to the first embodiment of the present invention, showing conductive connecting members and circuit.

FIG. 5 is a side view of a part of the sensitive layer according to the first embodiment of the present invention, showing conductive connecting members and circuit. As shown in FIG. 5, the sensitive layer 13 further comprises a first conductive connecting member 136, a second conducive connecting member 137, and a circuit connecting member 139. The first conductive connecting member 136, a second conducive connecting member 137, and a circuit connecting member 139 are connected with each other through wire or cable. In the present embodiment, the first conductive connecting member 136 is sandwiched between the first flexible thin-film plate 131 and the first conductive layer 133, and the second conductive connecting member 137 is sandwiched between the second flexible thin-film plate 132 and the second conductive layer 134. In some embodiments, the first conductive connecting member 136 may be inserted in the first conductive layer 133. In some embodiments, the second conductive connecting member 137 may be sandwiched between the intermediate layer 135 and the second conductive layer 134. In some embodiments, the second conductive connecting member 137 may be inserted in the second conductive layer 134. In some embodiments, the first and second conductive connecting members 136, 137 may be integrally formed. The circuit connecting member 139 is used for determining the connection between the first conductive layer 133 and the second conductive layer 134. Once the first conductive layer 133 is contacted with the second conductive layer 134, the circuit connecting member 139 will output a signal indicating that something or someone is currently on the mat. The circuit connecting member 139 may include a WIFI or Bluetooth unit to communicate with external server wirelessly. In some embodiments, the circuit connecting member 139 is programmable and is programmed with a delay function such that when there is a contact an alarm is delayed for a predetermined period. In some embodiments, the circuit connecting member 139 is integrated with a hummer to sound the alarm. The circuit connecting member 139 can be placed inside or outside the mat. For example, the circuit 139 may be disposed on the edge or at any other places in the mat.

Figure 6:
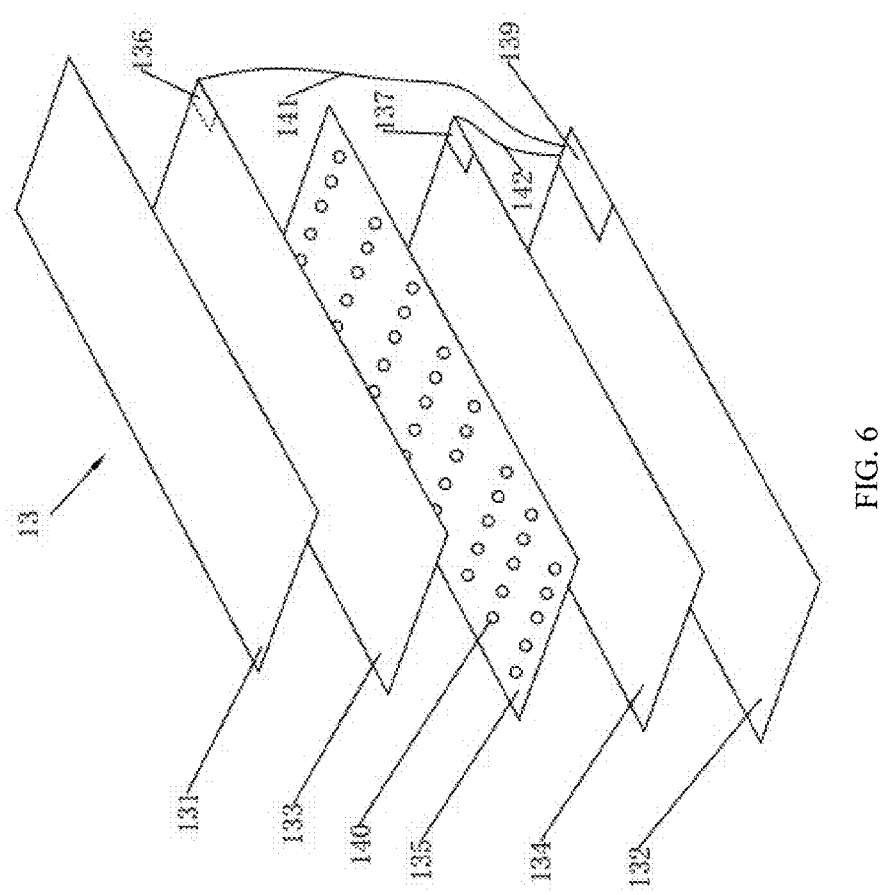
FIG. 6 is an exploded view of the sensitive layer according to the first embodiment of the present invention.

FIG. 6 is an exploded view of the sensitive layer according to the first embodiment of the present invention. As shown in FIG. 6, the first conductive connecting member 136, the second conducive connecting member 137, and the circuit 139 are disposed at the corner of the mat. Those skilled in the art should know that they can be disposed at any other places as needed. For example, each of the first and second conductive connecting members 136, 137 may be disposed along one side of the mat, or around the mat. The first conductive connecting member 136 is connected to the circuit via wire 141, and the second conducive connecting member 137 is connected to the circuit via wire 142. The wires 141, 142 may be dispose outside the mat or pass through a hole in the mat.

Figure 7:
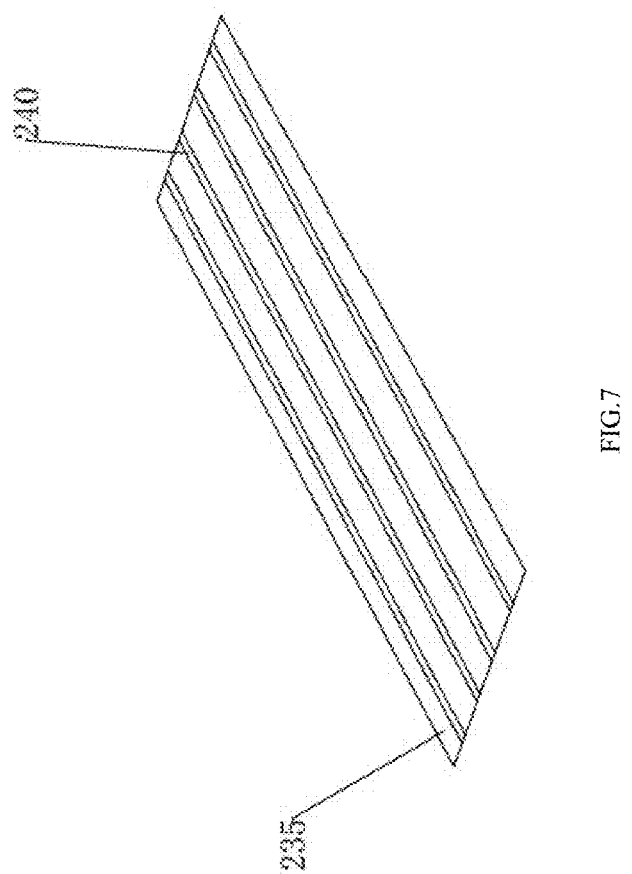
FIG. 7 is a schematic view of an intermediate layer according to the second embodiment of the present invention.

FIG. 7 is a schematic view of an intermediate layer according to the second embodiment of the present invention. As shown in FIG. 7, the intermediate layer 235 is provided with a plurality of parallel throughout slots such that the first and second conductive layers are contacted with each other and thus conduct when the sensitive layer is subjected to an external pressure. In some embodiments, other hollowed-out patterns are also possible as long as two conductive layers can be contacted with each other through the hollowed-out part under pressure.

Figure 8:
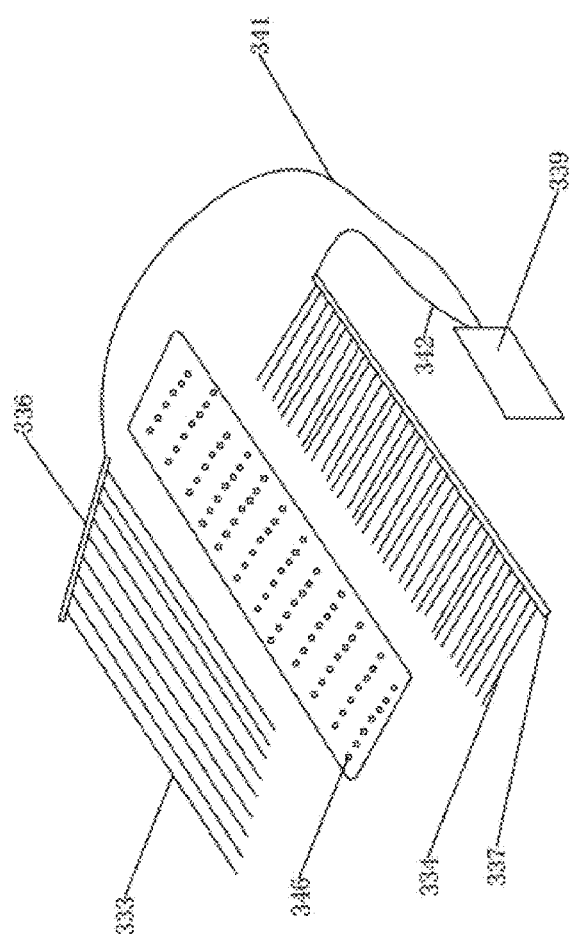
FIG. 8 is an exploded view of the combination of conductive layers and an intermediate layer according to the third embodiment of the present invention.
Figure 9:
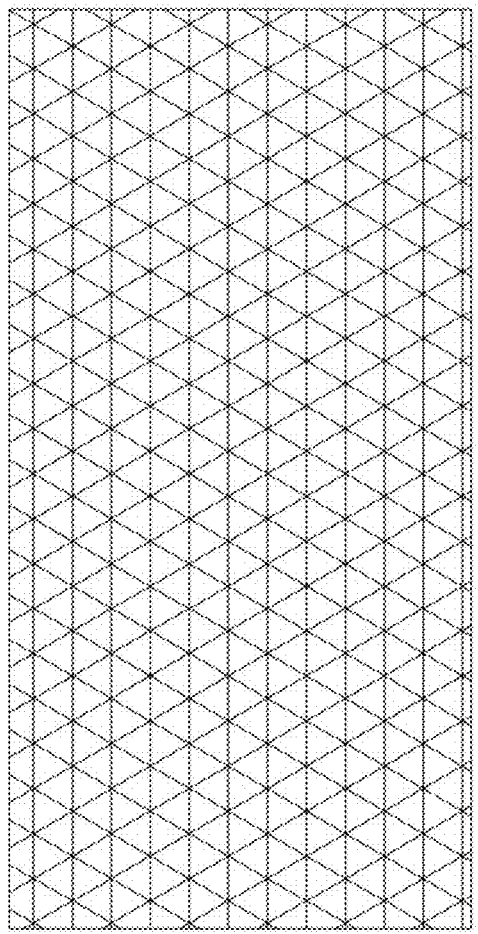
FIG. 9 is a plan view of a sensitive layer according to another embodiment of the present invention.

FIG. 8 is an exploded view of the combination of conductive layers and an intermediate layer according to the third embodiment of the present invention. As shown in FIG. 9, the first conductive layer 336 includes a plurality of wires 333 disposed along a first direction, and the second conductive layer 337 includes a plurality of wires 334 disposed along a second direction. The second direction is different from the first direction. For example, the second direction may be orthogonal to the first direction. Each of the wires 333 is connected to a first multiplexer 336, and each of the wires 334 is connected to a second multiplexer 337. The first and second multiplexers 336, 337 are connected to a control circuit 339 through wires 341, 342, respectively. In this embodiment, the intermediate layer 335 is provided with a plurality of through holes that are corresponding to and aligned with the crossover points of wires 333 and wires 334 such that the first conductive layer 333 and the second conductive layer 334 are contacted with each other and thus conduct when the sensitive layer is subjected to an external pressure. Those skilled in the art should know, the wires and holes in the sensing area can be formed into any shape as needed. FIG. 9 is a plan view of a sensitive layer according to another embodiment of the present invention. The number of touch points can be adjusted by changing the number of rows and columns of the wires or by programming the control circuit 339 to enable or disable some of the wires. In some embodiments, the alarm can be generated based on the number of touch points. The control circuit 339 can be programmed to accommodate different situations. In some embodiments, the control circuit 339 is programmable to enable and disable each of the plurality of wires of the first conductive layer and each of the plurality of wires of the second conductive layer such that the alarm signal can be generated by the control circuit based on contact at one or more predetermined intersections. For example, if the touch points in a small area (e.g., 5×15 cm$^2$) are triggered, this may mean that the patient is standing on the mat. If the touch points in a large area (e.g., 30×180 cm$^2$) are triggered, this may mean that the patient is lying down and the nursing system should sound alarm. In some embodiments, each mat has an identification (ID) stored in the circuit. This ID is transmitted to the server or the central unit of hospital along with touch triggered signals so that the server or the central unit can display which mat has been activated. In this embodiment, a multiple contact points on the mat can be detected by a multiple touch detection circuit. This way if a patient is sitting on the mat as a result of a fall from a bed, multiple touch points can be detected and patient's position on the map can be determined. The circuit can be programmed such that a single touch would not generate an alarm or a predetermined delay would be used. Alternatively, predetermined delay can be used for both a single and multiple touches. In some embodiments, the control circuit 339 is integrated with a wireless communication module through which the control circuit 339 can communicate with a remote apparatus. For example, the user can use the App on the remote apparatus to enable and disable any intersections as required.

Figure 10:
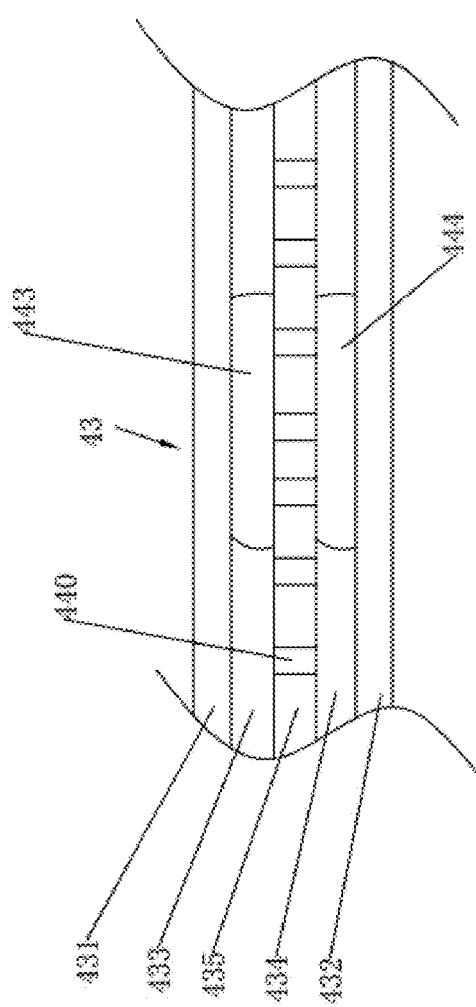
FIG. 10 is a side view of the sensitive layer in an unfolded state according to the fourth embodiment of the present invention.

FIG. 10 is a side view of the sensitive layer in an unfolded state according to the fourth embodiment of the present invention. As shown in FIG. 10, the first conductive layer 433 includes a first flexible conductive section 443, and the second conductive layer 434 includes a second flexible conductive section 444 that is aligned with the first flexible conductive section 443. The intermediate layer 435 is provided with a plurality of through holes 440 such that the first conductive plate 443 and the second conductive plate 444 can be contacted with each other and thus make the first conductive layer 433 and the second conductive layer 434 conduct when the sensitive layer is subjected to an external pressure.

Figure 11:
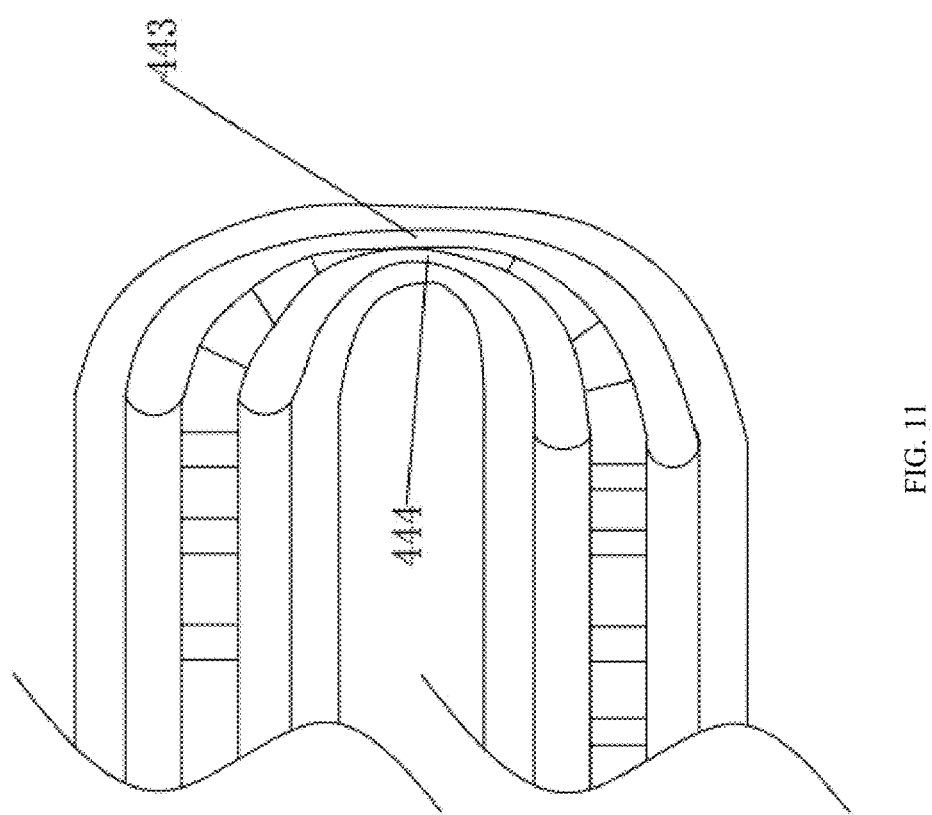
FIG. 11 is a side view of the sensitive layer in a folded state according to the fourth embodiment of the present invention.

FIG. 11 is a side view of the sensitive layer in a folded state according to the fourth embodiment of the present invention. As shown in FIG. 11, when the mat is folded, the first flexible conductive section 443 and the flexible second conductive layer 434 are contacted with each other though the through hole. The flexibility of the first and second flexible conductive sections 443, 444 ensures the normal functionality of conductive layers when folded.

Figure 12:
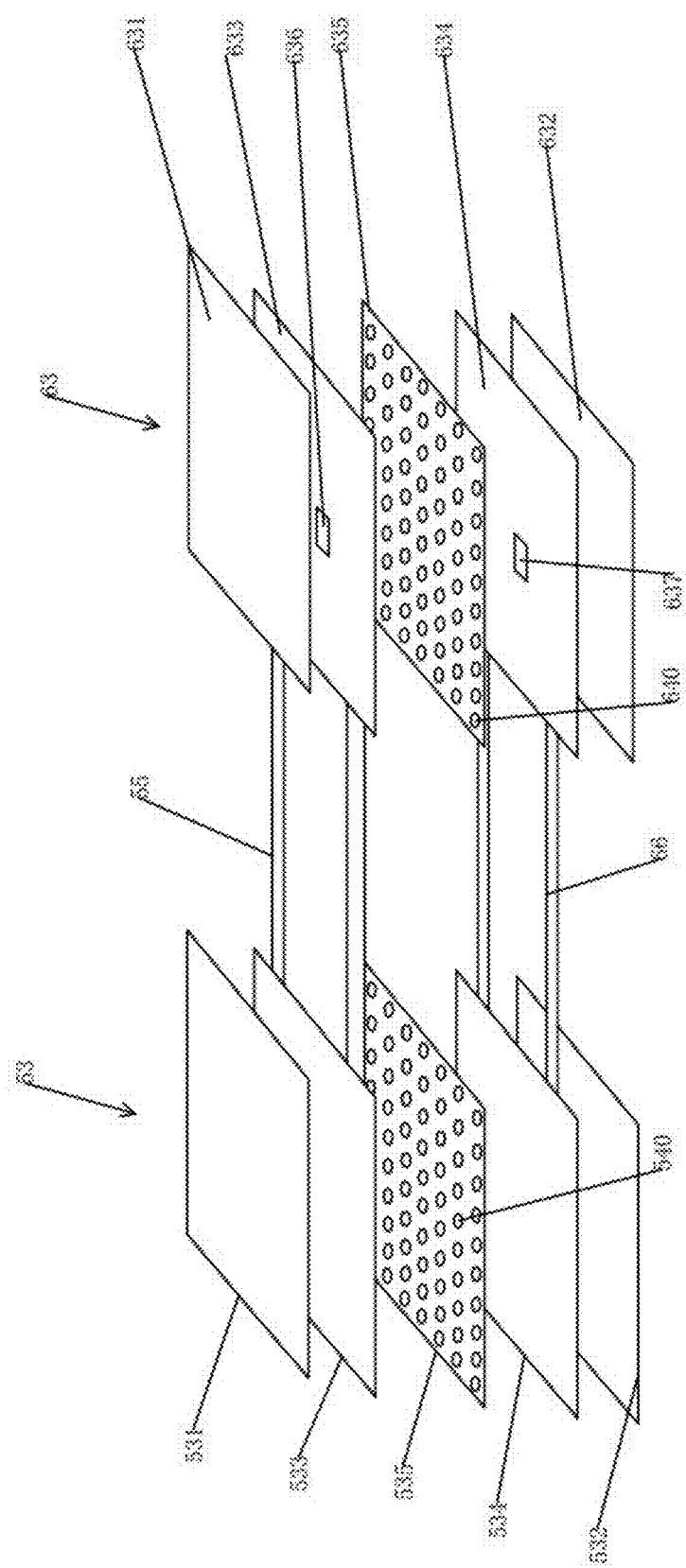
FIG. 12 is an exploded view of the sensitive layer according to the fifth embodiment of the present invention.

FIG. 12 is an exploded view of the sensitive layer according to the fifth embodiment of the present invention. As shown in FIG. 12, the sensitive layer includes a left part 53 and a right part 63. These two parts are connected with each other by special flexible circuit such that they can be folded together. The left part includes the top surface layer 531, the bottom surface layer 532, the first conductive layer 533, the second conductive layer 534, and the buffer layer 535. These layers are stacked in the order shown in FIG. 12. The buffer layer 535 is provided with a plurality of through holes 540 such that the first conductive layer 533 and the second conductive layer 534 are contacted with each other and thus conduct when the left part 53 of the sensitive layer is subjected to an external pressure. Similar to the left part, the right part includes the top surface layer 631, the bottom surface layer 632, the first conductive layer 633, the second conductive layer 634, and the buffer layer 635, which is stacked in the order shown in FIG. 12. The buffer layer 635 is provided with a plurality of through holes 640 such that the first conductive layer 633 and the second conductive layer 634 are contacted with each other and thus conduct when the right part 63 of the sensitive layer is subjected to an external pressure. In the present embodiments, the first conductive connecting member 636 and the second conducive connecting member 637 are disposed on the first conductive layer 633 and the second conductive layer 634, respectively. However, those skilled in the art should know that they can be disposed at any other places as needed. The first conductive layer 533 and the first conductive layer 633 are connected with each other through one or more first flexible circuits 55, while second conductive layer 534 and the second conductive layer 634 are connected with each other through one or more second flexible circuits 66. Each of the first flexible circuits 55 does not overlap with or contact with each of the second flexible circuits 66. In the present embodiments, there are two first flexible circuits 55 and two second flexible circuits 66.

Figure 13:
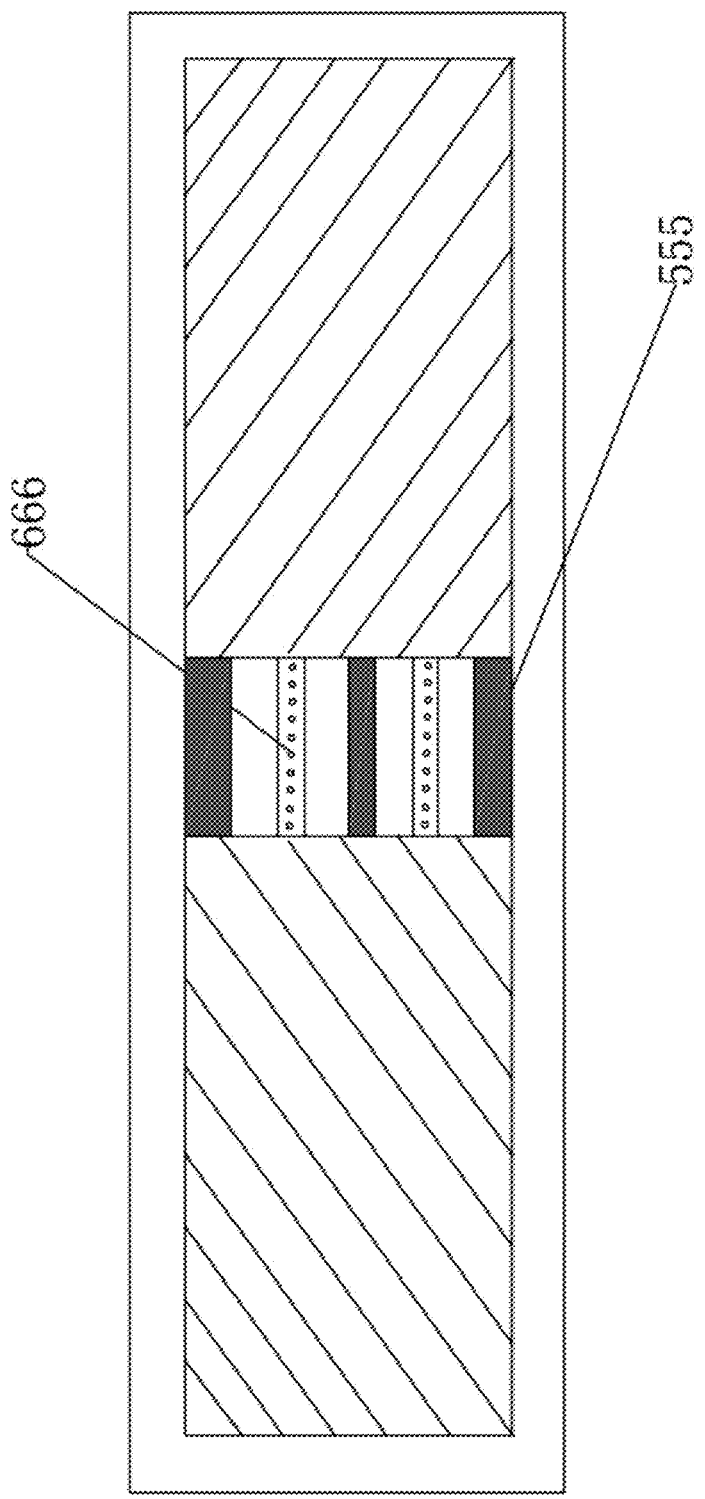
FIG. 13 is a top view of the sensitive layer according to the sixth embodiment of the present invention.

FIG. 13 is a top view of the sensitive layer according to the sixth embodiment of the present invention. In this embodiment, the first conductive layers on the left and right sides are connected with each other through three first flexible circuits 555, while the second conductive layers are connected with each other through two second flexible circuits 666. Each of the first flexible circuits 555 does not overlap with or contact with each of the second flexible circuits 666. Each of the first flexible circuits 555 and each of the second flexible circuits 666 are located in different planes.

Figure 14:
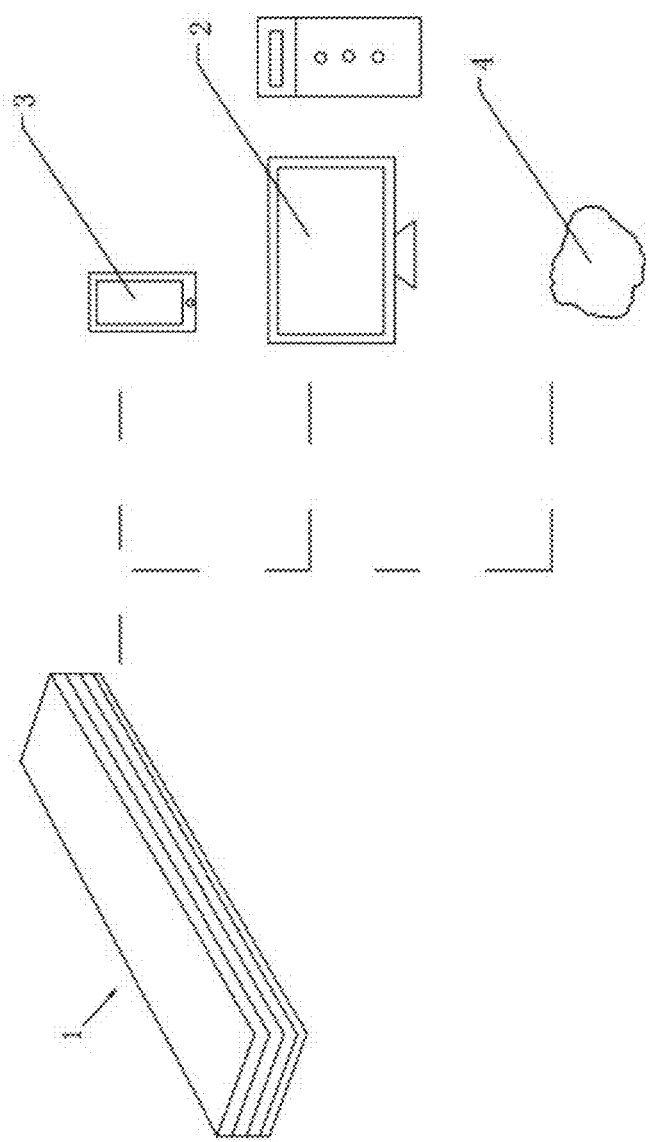
FIG. 14 is a schematic view of an alarm system including the anti-slip cushioning sensor mat of the present invention.

FIG. 14 is a schematic view of an alarm system including the anti-slip cushioning sensor mat of the present invention. As shown in FIG. 14, the alarm system includes the anti-slip cushioning sensor mat 1 and a server. The server, for example, can be a portable device 2 such as a smartphone, a smartwatch, a lap-top, a desktop computer 3, a database, or a cloud sever 4, and so on. The anti-slip cushioning sensor mat 1 is used for detecting contact and output signal to the server. The server then determines whether to sound alarm depending on the preset criteria.

Figure 15:
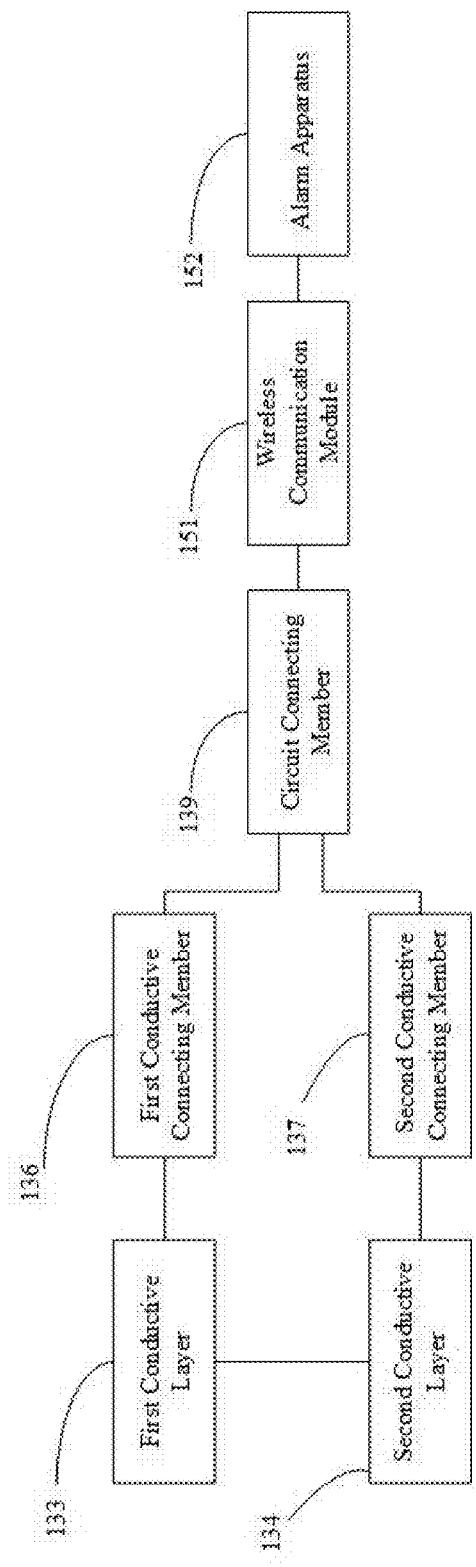
FIG. 15 is an operative process of the alarm system according to one embodiment of the present invention.

FIG. 15 is an operative process of the alarm system according to one embodiment of the present invention. In this embodiment, an alarm system comprises an anti-slip cushioning sensor mat configured to detect the presence of a subject and send a signal when the subject is present, and an alarm apparatus connected to the sensitive layer and configured to receive the alarm signal and sound alarm. The structure of the anti-slip cushioning sensor mat is the same as that described according to the first embodiment (FIG. 5) and is omitted here. As shown in FIG. 15, when the first conductive layer 133 and the second conductive layer 134 contact with each other due to an external pressure on the anti-slip cushioning sensor mat, a closed loop circuit will be formed by the first conductive layer 133, the second conductive layer 134, the first conductive connecting member 136, the second conductive connecting member 137, and the circuit connecting member 139 such that an alarm signal (i.e., conducting signal) indicating that the anti-slip cushioning sensor mat is under pressure, i.e., the subject is present, will be generated by the circuit connecting member 139 and output to the wireless communication module 151, which further transmits the signal to an alarm apparatus 152 wirelessly. The alarm apparatus 152 could be a smartphone, a remote server, a cloud database, and so on. In some embodiments, the circuit connecting member 139 can be directly connected to a control center through cable.

Figure 16:
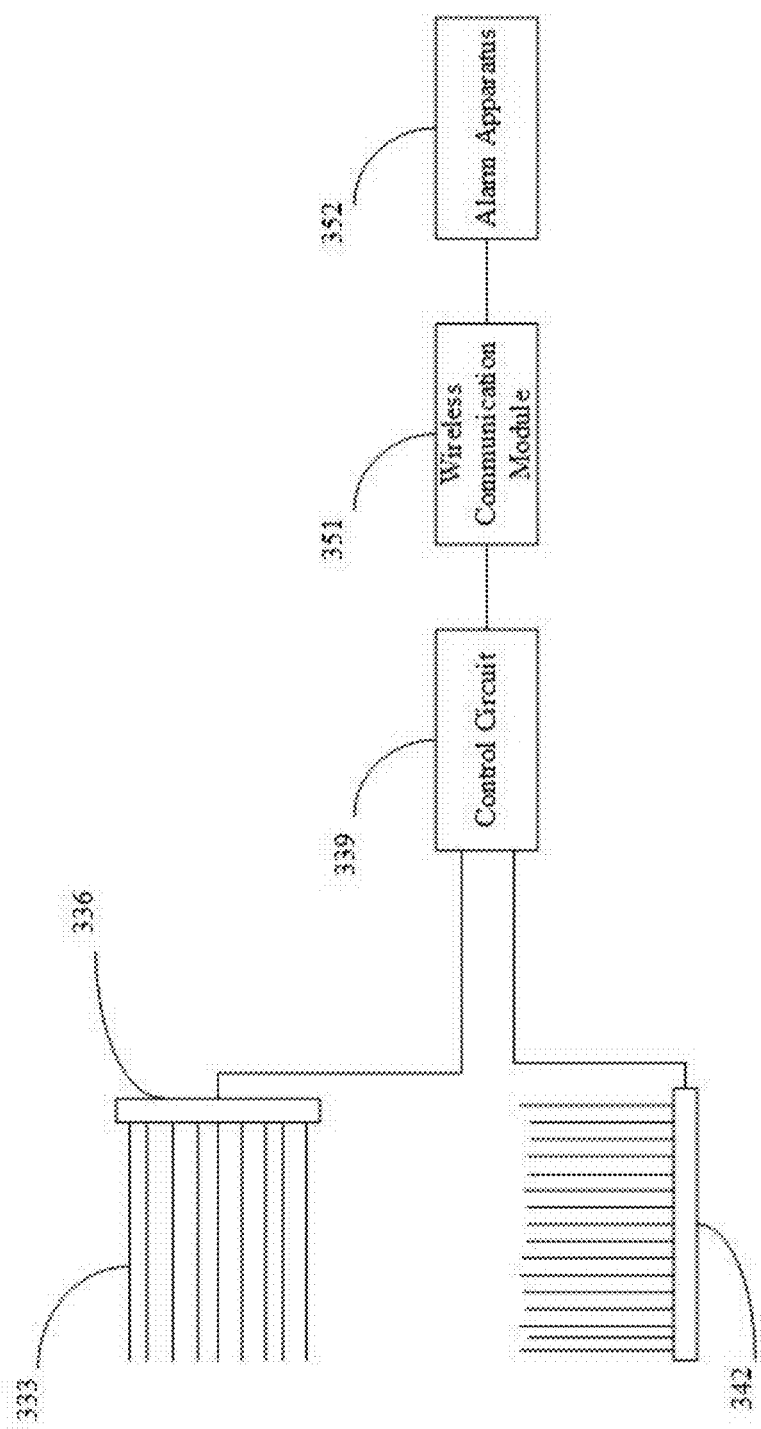
FIG. 16 is an operative process of the alarm system according to another embodiment of the present invention.

FIG. 16 is an operative process of the alarm system according to another embodiment of the present invention. In this embodiment, an alarm system comprises an anti-slip cushioning sensor mat configured to detect the presence of a subject and send a signal when the subject is present, and an alarm apparatus connected to the sensitive layer and configured to receive the alarm signal and sound alarm. The structure of the anti-slip cushioning sensor mat is the same as that described according to the third embodiment (FIG. 7) and is omitted here. As shown in FIG. 16, when the first conductive layer 333 and the second conductive layer 334 contact with each other due to an external pressure on the anti-slip cushioning sensor mat, at least one closed loop circuit will be formed by the first conductive layer 333, the second conductive layer 334, the first multiplexer 336, the second multiplexer 337, and the control circuit 339 such that an alarm signal (i.e., conducting signal) indicating that the anti-slip cushioning sensor mat is under pressure, i.e., the subject is present, will be generated by the control circuit 339 connecting member and output to the wireless communication module 351, which further transmits the signal to an alarm apparatus 352 wirelessly. The alarm apparatus 352 could be a smartphone, a remote server, a cloud database, and so on. In some embodiments, the control circuit 339 can be directly connected to a control center through cable. In some embodiments, the user can use an APP on his cellphone to program the control circuit 339 so as to enable and disable each of the plurality of wires of the first conductive layer and each of the plurality of wires of the second conductive layer such that the alarm signal can be generated by the control circuit based on contact at one or more predetermined intersections. In some embodiments, the user can use the APP to set a delay setting instruction to the control circuit 339 through the wireless communication module 351 to make the alarm delayed for a predetermined period. The circuit described in FIG. 14 is capable of detecting multiple touches on the mat. The control circuit is configured to detect multiple touches and determine the location of the touches on the mat. The location information can be sent to the alarm apparatus 352. Furthermore, a delay circuit can be implemented such that a delay can be introduced to prevent false touches on the mat. The delay amount can be adjusted by an application program which communicates with the control circuit. Communication can be wired or wireless communication.

Although the present invention has been described with reference to the preferred embodiments, it is apparent to those skilled in the art that a variety of modification and changes may be made without departing from the scope of the patent for invention which is intended to be defined by the appended claims.

I claim:
1. An anti-slip cushioning sensor mat, comprising:
   a PVC leather layer;
   a polyurethane foaming layer disposed below the PVC leather layer;
   a sensitive layer disposed below the polyurethane foaming layer; and
   a rubber layer disposed below the sensitive layer;
   wherein
   the sensitive layer further comprises:
   a first flexible thin-film plate;
   a first conductive layer disposed below the first flexible thin-film plate;
   a first intermediate layer disposed below the first conductive layer;
   a second conductive layer disposed below the first intermediate layer; and
   a second flexible thin-film plate disposed below the second conductive layer.

2. The anti-slip cushioning sensor mat of claim 1, wherein the first conductive layer is formed by printing or coating ink made of copper or conductive graphite on the first flexible thin-film plate, and the second conductive layer is formed by printing or coating the ink on the second flexible thin-film plate.

3. The anti-slip cushioning sensor mat of claim 1, wherein the first intermediate layer is made of a low-density elastic material and provided with a plurality of through holes such that the first conductive layer and the second conductive layer are contacted with each other when the anti-slip cushioning sensor mat is subjected to a pressure.

4. The anti-slip cushioning sensor mat of claim 3, wherein at least one vent is provided on at least one of the first flexible thin-film plate and the second flexible thin-film plate.

5. The anti-slip cushioning sensor mat of claim 3, wherein the first conductive layer includes a plurality of wires disposed in a first direction and each connected to a first multiplexer, and the second conductive layer includes a plurality of wires disposed in a second direction and each connected to a second multiplexer, the plurality of through holes of the first intermediate layer are aligned with intersections formed by the plurality of wires of the first conductive layer and the plurality of wires of the second conductive layer, wherein the second direction is different from the first direction.

6. The anti-slip cushioning sensor mat of claim 5, wherein the first multiplexer and the second multiplexer are connected to a control circuit, the control circuit is programmable to enable and disable each of the plurality of wires of the first conductive layer and each of the plurality of wires of the second conductive layer.

7. The anti-slip cushioning sensor mat of claim 3, wherein the first conductive layer includes a first flexible conductive section and the second conductive layer includes a second flexible conductive section such that the first flexible conductive section is contacted with the second flexible plate when the sensitive layer is folded at the place where the first flexible conductive section and the second flexible conductive section are located.

8. The anti-slip cushioning sensor mat of claim 1, wherein the sensitive layer further comprises:
   a first conductive connecting member connected to the first conductive layer,
   a second conductive connecting member connected to the second conductive layer, and
   a circuit connection member connected to the first conductive connecting member and the second conductive connecting member.

9. The anti-slip cushioning sensor mat of claim 8, wherein the first conductive connecting member is disposed between the first conductive layer and the first intermediate layer, and the second conductive connecting member is disposed between the second conductive layer and the first intermediate layer.

10. The anti-slip cushioning sensor mat of claim 1, wherein the first intermediate layer is provided with a plurality of parallel through-slots such that the first conductive layer and the second conductive layer are contacted with each other when the anti-slip cushioning sensor mat is subjected to a pressure.

11. The anti-slip cushioning sensor mat of claim 1, wherein the sensitive layer further comprises:
   a third flexible thin-film plate;
   a third conductive layer disposed below the third flexible thin-film plate;
   a second intermediate layer disposed below the third conductive layer;
   a fourth conductive layer disposed below the second intermediate layer;
   a fourth flexible thin-film plate disposed below the fourth conductive layer; and
   the second intermediate layer is provided with a plurality of through holes such that the third conductive layer and the fourth conductive layer contact with each other when the anti-slip cushioning sensor mat is subjected to a vertical force.

12. The anti-slip cushioning sensor mat of claim 11, wherein the first conductive layer is connected with the third conductive layer through at least one first flexible circuit, and the second conductive layer is connected with the fourth conductive layer through at least one second flexible circuit.

13. An alarm system, comprising:
   an anti-slip cushioning sensor mat configured to detect the presence of a subject and send a signal when the subject is present, wherein the anti-slip cushioning sensor mat comprises:
   a PVC leather layer;
   a polyurethane foaming layer disposed below the PVC leather layer;

a sensitive layer disposed below the polyurethane foaming layer and configured to sense whether the subject is present and output an alarm signal when the subject is present; and a rubber layer disposed below the sensitive layer;

wherein the sensitive layer further comprises:

a first flexible thin-film plate;

a first conductive layer disposed below the first flexible thin-film plate;

an intermediate layer disposed below the first conductive layer;

a second conductive layer disposed below the intermediate layer; and a second flexible thin-film plate disposed below the second conductive layer;

wherein the intermediate layer is made of a low-density elastic material and provided with a plurality of through holes such that the first conductive layer and the second conductive layer are contacted with each other when the anti-slip cushioning sensor mat is subjected to a pressure; and an alarm apparatus connected to the sensitive layer and configured to receive the alarm signal and sound alarm.

14. The alarm system of claim 13, wherein the alarm apparatus is a wireless communication apparatus, and wherein the sensitive layer further comprises:

a first conductive connecting member connected to the first conductive layer, a second conductive connecting member connected to the second conductive layer, a circuit connection member connected to the first conductive connecting member and the second conductive connecting member, a wireless communication module connected to the circuit connection member and configured to generate and transmit the alarm signal wirelessly to the wireless communication apparatus once the anti-slip cushioning sensor mat is subjected to a pressure.

15. The alarm system of claim 13, wherein the first conductive layer includes a plurality of wires disposed in a first direction and each connected to a first multiplexer, and the second conductive layer includes a plurality of wires disposed in a second direction and each connected to a second multiplexer, the plurality of through holes of the intermediate layer are aligned with intersections formed by the plurality of wires of the first conductive layer and the plurality of wires of the second conductive layer, wherein the second direction is different from the first direction.

16. The alarm system of claim 15, wherein the first multiplexer and the second multiplexer are connected to a control circuit, the control circuit is programmable to enable and disable each of the plurality of wires of the first conductive layer and each of the plurality of wires of the second conductive layer such that the alarm signal can be generated by the control circuit based on contact at one or more predetermined intersections.

17. The alarm system of claim 16, wherein the alarm apparatus is a wireless communication apparatus, and wherein the sensitive layer further comprises a wireless communication module connected to the control circuit and configured to wirelessly transmit the alarm signal generated by the control circuit to the wireless communication apparatus.

18. A method of making an anti-slip cushioning sensor mat, comprising the following steps:

putting PVC leather into a mold;

injecting polyurethane mixed foaming material into the mold to generate a complex multilayer structure including a PVC leather layer and a polyurethane foaming layer;

attaching a sensitive layer to the polyurethane foaming layer; and adhering a rubber layer to the sensitive layer.

* * * * *